(12) United States Patent
Uchida et al.

(10) Patent No.: US 11,415,583 B2
(45) Date of Patent: Aug. 16, 2022

(54) METHOD, KIT, AND APPARATUS FOR CANCER DETECTION USING URINARY TUMOR MARKERS

(71) Applicants: National University Corporation Nagoya University, Aichi (JP); Hitachi, Ltd., Tokyo (JP)

(72) Inventors: Hiroo Uchida, Aichi (JP); Akinari Hinoki, Aichi (JP); Minoru Sakairi, Tokyo (JP); Mayumi Abe, Tokyo (JP)

(73) Assignees: NATIONAL UNIVERSITY CORPORATION NAGOYA UNIVERSITY, Aichi (JP); HITACHI, LTD., Tokyo (JP)

(*) Notice: Subject to any disclaimer, the term of this patent is extended or adjusted under 35 U.S.C. 154(b) by 335 days.

(21) Appl. No.: 16/675,109

(22) Filed: Nov. 5, 2019

(65) Prior Publication Data
US 2020/0150124 A1 May 14, 2020

(30) Foreign Application Priority Data

Nov. 12, 2018 (JP) .............................. JP2018-212341

(51) Int. Cl.
| | |
|---|---|
| G01N 33/574 | (2006.01) |
| G16H 50/30 | (2018.01) |
| G16B 40/10 | (2019.01) |
| G01N 30/06 | (2006.01) |
| G01N 30/02 | (2006.01) |

(52) U.S. Cl.
CPC ....... *G01N 33/57484* (2013.01); *G01N 30/06* (2013.01); *G01N 33/57407* (2013.01); *G16B 40/10* (2019.02); *G16H 50/30* (2018.01); *G01N 2030/027* (2013.01); *G01N 2030/065* (2013.01); *G01N 2030/067* (2013.01)

(58) Field of Classification Search
CPC ............ G01N 33/57484; G01N 30/06; G01N 33/57407; G01N 2030/027; G01N 2030/065; G01N 2030/067; G01N 33/5011; G01N 2800/52; G01N 2800/56; G01N 2800/60; G16B 40/10; G16H 50/30
See application file for complete search history.

(56) References Cited

U.S. PATENT DOCUMENTS

| | | | |
|---|---|---|---|
| 2017/0003294 A1* | 1/2017 | Wang | ............... G01N 33/92 |
| 2019/0293653 A1 | 9/2019 | Uchida et al. | |

FOREIGN PATENT DOCUMENTS

JP    H05113438 A    5/1993

OTHER PUBLICATIONS

Verly et al., "Catecholamines profiles at diagnosis: Increased diagnostic sensitivity and correlation with biological and clinical features in nueroblastoma patients," European Journal of Cancer, vol. 72, pp. 235-243, publ. Jan. 4, 2017, DOI: 10.1016/j.ejca.2016.12.002. (Year: 2017).*

(Continued)

*Primary Examiner* — Jennifer Wecker
*Assistant Examiner* — Michael Paul Shimek
(74) *Attorney, Agent, or Firm* — Procopio, Cory, Hargreaves & Savitch LLP

(57) ABSTRACT

Provided are a method, an apparatus, and a kit for detecting a neuroblastoma in a subject and/or for monitoring a therapeutic effect on the neuroblastoma, by measuring a urinary tumor marker(s) in a sample from the subject.

13 Claims, 5 Drawing Sheets

(56) References Cited

OTHER PUBLICATIONS

Lam, et al., "Clinical validation of urine 3-methoxytyramine as a biomarker of neuroblastoma and comparison with other catecholamine-related biomarkers," Annals of Clinical Biochemistry, The Assoc. for Clin. Biochem. & Lab. Med., vol. 54(2), pp. 264-272, publ. May 22, 2016, DOI:10.1177/0004563216654723. (Year: 2016).*

Partial European Search Report for related European Application No. EP19207022.5 dated Apr. 7, 2020 (18 pages).

Lam, L. et al. "Clinical Validation of Urine 3-Methoxytyramine as a Biomarker of Neuroblastoma and Comparison with Other Catecholamine-Related Biomarkers" Annals of Clinical Biochemistry, May 22, 2016, pp. 264-272, vol. 54, No. 2.

Verly, I. et al. "Catecholamines Profiles at Diagnosis: Increased Sensitivity and Correlation with Biological and Clinical Features in Neuroblastoma Patients" European Journal of Cancer, Jan. 4, 2017, pp. 235-243, vol. 72.

Seeger, R. et al. "Neuroblastoma: Clinical Perspectives, Monoclonal Antibodies, and Retinoic Acid" UCLA Conference, 1982, pp. 873-884.

Mindikoglu, A. et al. "Unique Metabolomic Signature Associated with Hepatorenal Dysfunction and Mortality in Cirrhosis" Translational Research, May 2018, pp. 25-47, vol. 195.

* cited by examiner

METHOD, KIT, AND APPARATUS FOR CANCER DETECTION USING URINARY TUMOR MARKERS

RELATED APPLICATION

This application claims the benefit of priority to Japanese Patent Application number 2018-212341, filed Nov. 12, 2018, hereby incorporated by reference in its entirety.

TECHNICAL FIELD

The present invention relates to methods, kits, and apparatuses for detecting a neuroblastoma in a subject using urinary tumor markers derived from the subject.

BACKGROUND ART

Neuroblastoma is one of childhood cancers and is often diagnosed at 0 to 4 years of age. Neuroblastoma tumor cells produce catecholamine, which is a neurotransmitter, and the catecholamine converts into vanillylmandelic acid (VMA) and homovanillic acid (HVA), and they are excreted into the urine. Neuroblastoma mass screening examination that detects or determines VMA and HVA has been performed on six-month-old infants as subjects, to detect neuroblastoma early. Unfortunately, questions remain as to the efficacy of the examination (for example, Japanese Unexamined Patent Application Publication No. Hei 5(1993)-113438), and the examination is now suspended. Specifically, the examination does not contribute to effectively decreased mortality; and excessive examination and therapy becomes a problem, because some neuroblastoma have a good prognosis, and may spontaneously regress.

SUMMARY OF INVENTION

It has been generally verified that such a neuroblastoma, which is a childhood cancer, has a better outcome when treated in an earlier stage, and has a prognosis directly affected with early detection. This demands establishment of a precise, noninvasive examination method.

Urinary metabolites are less affected by enzymes as compared with blood substances, are structurally stable, and have sufficient possibilities to function as tumor markers. In addition, such urinary markers are very accessible also for cancer screening, because they are sampled from the urine, which can be easily collected even from children. Accordingly, the present invention has an object to identify a novel urinary tumor marker for neuroblastoma and to use the marker in detection of neuroblastoma typically in cancer examinations.

Solution to Problem

The present inventors have searched for urinary tumor markers for childhood cancers and, during this process, have found, of markers whose levels are high in neuroblastoma, markers whose levels are seldom high in stage 4S neuroblastoma-affected children, and, finally, have identified urinary tumor markers for determining stage 4S neuroblastoma-affected children, who have a good prognosis.

Specifically, the present invention relates to methods, apparatuses, and kits for neuroblastoma detection in a subject and/or for monitoring a therapeutic effect on the neuroblastoma, by measuring urinary metabolites serving as urinary tumor markers.

In an asepect, the present disclosure provides a method for detecting a neuroblastoma, the method including: measuring a urinary tumor marker in a urine sample derived from a subject, the step including:

measuring at least one urinary tumor marker selected from Group (A) as follows:
(A) 3-methoxytyramine sulfate, xanthopterin, vanillactate, 3,4-dihydroxyphenyl acetate, cystathionine, cortisol 21-glucuronide, 3,4-dihydroxyphenylacetate sulfate, cortisol, 3-methoxytyrosine, and 3-methoxytyramine; and measuring at least one urinary tumor marker selected from Group (B) as follows:
(B) 2-hydroxy-3-methylvalerate, vanillylmandelate, homovanillate, 3-methoxy-4-hydroxyphenyl glycol, and 3-(4-hydroxyphenyl)lactate; and detecting a neuroblastoma in the subject based on results of the measurement.

When the at least one Group (A) urinary tumor marker level is higher than a reference level, the method indicates that the subject is positive for a neuroblastoma and in a stage other than stage 4S.

When the at least one Group (A) urinary tumor marker level is lower than the reference level, but the at least one Group (B) urinary tumor marker level is higher than a reference level, the method indicates that the subject is positive for a neuroblastoma and is in stage 4S.

In another aspect, the present disclosure provides an apparatus for detecting a neuroblastoma, the apparatus including:

a measuring unit which is configured to measure a urinary tumor marker in a urine sample, the measuring unit measuring:

at least one urinary tumor marker selected from Group (A) as follows:
(A) 3-methoxytyramine sulfate, xanthopterin, vanillactate, 3,4-dihydroxyphenyl acetate, cystathionine, cortisol 21-glucuronide, 3,4-dihydroxyphenylacetate sulfate, cortisol, 3-methoxytyrosine, and 3-methoxytyramine; and at least one urinary tumor marker selected from Group (B) as follows:
(B) 2-hydroxy-3-methylvalerate, vanillylmandelate, homovanillate, 3-methoxy-4-hydroxyphenyl glycol, and 3-(4-hydroxyphenyl)lactate;

a comparing unit which is configured to compare a measured value of the urinary tumor marker measured by the measuring unit with a corresponding reference level or previous measured value; and a determining unit which is configured to detect a neuroblastoma based on comparison results obtained by the comparing unit.

In still another aspect, the present disclosure provides a kit for detecting a neuroblastoma, the kit including:

a means for measuring at least one urinary tumor marker selected from Group (A) as follows:
(A) 3-methoxytyramine sulfate, xanthopterin, vanillactate, 3,4-dihydroxyphenylacetate, cystathionine, cortisol 21-glucuronide, 3,4-dihydroxyphenylacetate sulfate, cortisol, 3-methoxytyrosine, and 3-methoxytyramine; and a means for measuring at least one urinary tumor marker selected from Group (B) as follows:
(B) 2-hydroxy-3-methylvalerate, vanillylmandelate, homovanillate, 3-methoxy-4-hydroxyphenyl glycol, and 3-(4-hydroxyphenyl)lactate.

In yet another aspect, the present disclosure provides a method for evaluating the efficacy of a neuroblastoma therapy, the method including:

measuring a urinary tumor marker in a urine sample derived from an animal with a neuroblastoma, the animal having undergone a treatment with a test therapeutic agent or therapy by measuring:

at least one urinary tumor marker selected from Group (A) as follows:
(A) 3-methoxytyramine sulfate, xanthopterin, vanillactate, 3,4-dihydroxyphenyl acetate, cystathionine, cortisol 21-glucuronide, 3,4-dihydroxyphenylacetate sulfate, cortisol, 3-methoxytyrosine, and 3-methoxytyramine, and at least one urinary tumor marker selected from Group (B) as follows:
(B) 2-hydroxy-3-methylvalerate, vanillylmandelate, homovanillate, 3-methoxy-4-hydroxyphenyl glycol, and 3-(4-hydroxyphenyl)lactate; and evaluating efficacy of the test therapeutic agent or therapy on the neuroblastoma based on the measurement results.

The present invention provides a method, an apparatus, and a kit for easily and inexpensively detecting a neuroblastoma with minimal invasion. In particular, the method, apparatus, and kit can determine whether the neuroblastoma is stage 4S neuroblastoma, which has a good prognosis. This can avoid unnecessary therapy and examination and can select an appropriate therapy for a neuroblastoma other than stage 4S neuroblastoma. The examination performed is an examination using urine. This extremely simplifies the collection or sampling technique in clinical site and significantly increases the convenience of medical care workers. The present invention is therefore useful in the fields typically of diagnosis, examination, therapy evaluation, and drug development for neuroblastoma.

DETAILED DESCRIPTION

Figure 1:
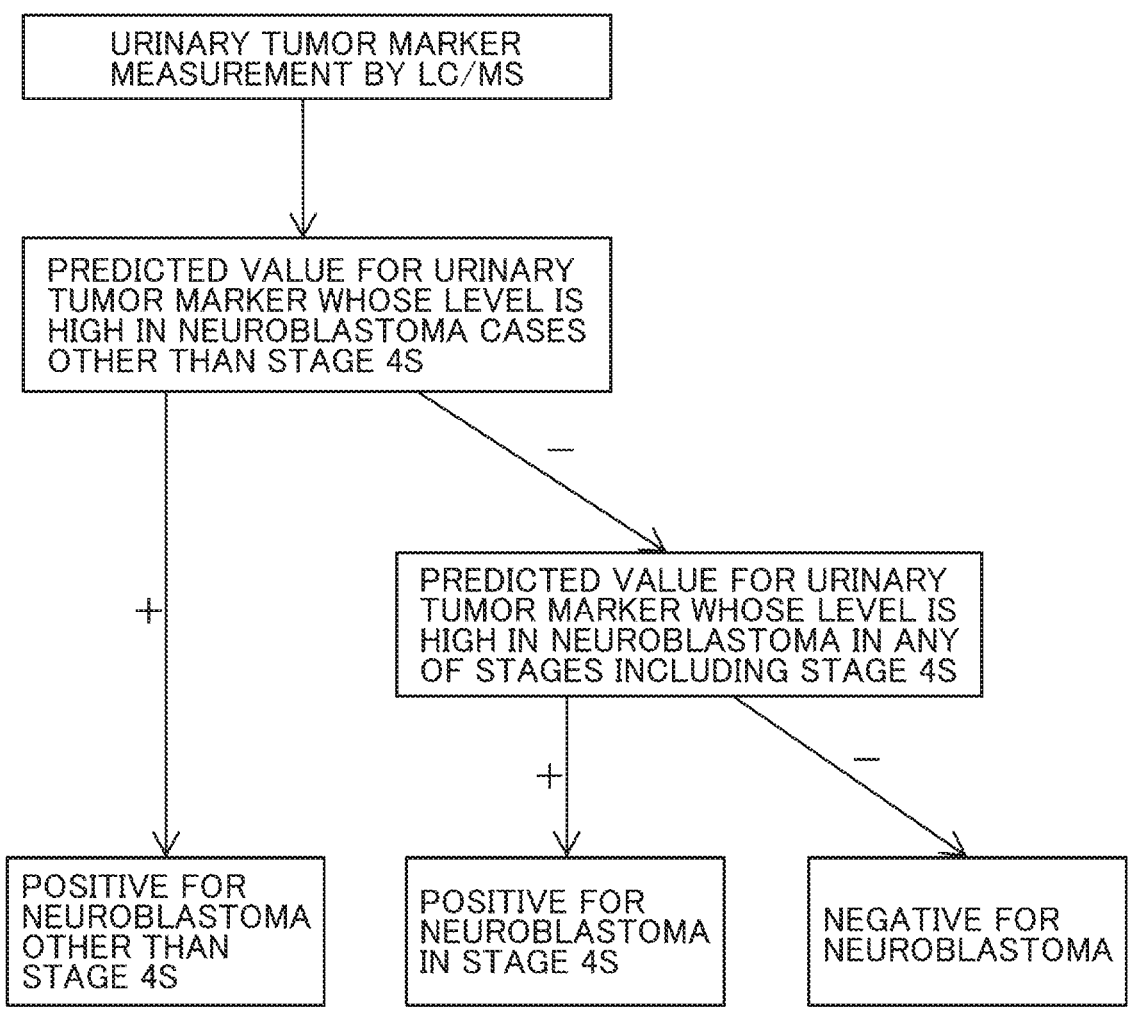
FIG. 1 is an exemplary flow chart of neuroblastoma detection using urinary tumor markers, to which the present invention is applied.

A method, an apparatus, and a kit according to the present invention utilize a novel urinary tumor markers and marker groups which relate to neuroblastoma, especially which can distinguish stage 4S neuroblastoma from neuroblastoma other than stage 4S neuroblastoma. These urinary tumor markers are metabolites that vary in their urinary levels with development and progression of neuroblastoma and/or before and after treatment of neuroblastoma and, in particular, differ in urinary levels between stage 4S neuroblastoma and neuroblastoma in a stage other than stage 4S. The urinary tumor markers may be useful typically for neuroblastoma detection, neuroblastoma risk prediction, neuroblastoma stage determination, neuroblastoma prognosis determination, and/or monitoring of therapeutic effects on neuroblastoma.

The neuroblastoma detection method according to an embodiment of the present invention includes a step of measuring a urinary tumor marker in a urine sample derived from a subject, and a step of detecting a neuroblastoma in the subject on the basis of the measurement result. The measuring step measures a urinary tumor marker whose level is high in a neuroblastoma other than stage 4S neuroblastoma (hereinafter also referred to as a "marker specific to neuroblastoma other than stage 4S neuroblastoma" or a "Group (A) marker"), as needed in combination with a urinary tumor marker whose level is high in a neuroblastoma in any of stages including stage 4S (hereinafter also referred to as a "marker detected in a neuroblastoma in any of stages including stage 4S" or "Group (B) marker"). When the Group (A) marker is detected at a level higher than a reference level, the subject can be determined to be affected with a neuroblastoma other than stage 4S neuroblastoma. When the Group (A) marker level is lower than the reference level and the Group (B) marker level is higher than a reference level, the subject can be determined to be affected with a neuroblastoma in stage 4S. In contrast, when both the Group (A) marker and the Group (B) marker are at levels lower than the reference levels, the subject can be determined to be negative for neuroblastoma.

According to the present invention, a neuroblastoma is a detection target. The neuroblastoma is a kind of childhood cancers and is known to emerge typically from the sympathetic ganglion and the adrenal medulla. Cancers may encompass primary, metastatic, and recurrent cancers and are classified into several stages based on their progression degrees and expanses. Cancers of different categories, i.e., primary, metastatic, and recurrent cancers, and cancers in different stages require different treatments (therapeutic approaches).

Neuroblastoma staging is generally performed on the basis of International Neuroblastoma Staging System (INSS) (for example, Brodeur et al., J Clin Oncol, vol. 11, pp. 1466-1477, 1993):

TABLE 1

INSS Staging

| Stage | Definition |
|---|---|
| 1 | Localized tumor with complete gross excision, with or without microscopic residual disease; representative ipsilateral lymph nodes negative for tumor microscopically (nodes attached to and removed with the primary tumor may be positive). |
| 2A | Localized tumor with incomplete gross excision; representative ipsilateral nonadherent lymph nodes negative for tumor microscopically. |
| 2B | Localized tumor with or without complete gross excision, with ipsilateral nonadherent lymph nodes positive for tumor. Enlarged contralateral lymph nodes must be negative microscopically. |
| 3 | Unresectable unilateral tumor infiltrating across the midline (vertebral column), with or without regional lymph node involvement; or localized unilateral tumor with contralateral regional lymph node involvement; or midline tumor with bilateral extension by infiltration (unresectable) or by lymph node involvement. |

TABLE 1-continued

INSS Staging

| Stage | Definition |
|---|---|
| 4 | Any primary tumor with dissemination to distant lymph nodes, bone, bone marrow, liver, skin, and/or other organs (except as defined for stage 4S). |
| 4S | Localized primary tumor, as defined for stage 1, 2A, or 2B, with dissemination limited to skin, liver, and/or bone marrow (by definition limited to infants younger than 12 months). Marrow involvement should be minimal, i.e., less than 10% of total nucleated cells. More extensive marrow involvement would be considered to be stage 4. The results of the MIBG scintigraphy, if performed, should be negative in the marrow. |

According to the present invention, of neuroblastoma, a neuroblastoma in stage 4S, and neuroblastoma in a stage other than stage 4S may be distinguished and detected individually. The stage 4S neuroblastoma is observed in infants (in particular, infants under 12 months of age) and is a special group of neuroblastoma in which the tumor itself is in stages 1 to 2B, but undergoes metastasis limited to skin, liver, and/or bone marrow and also undergoes distant metastasis, but spontaneously regresses without treatment, and has a good prognosis. A study reports that stage 4S patients are observed in a proportion of about 8% of neuroblastoma-affected infants (under 12 months of age) (Ikeda et al., British Journal of Cancer, vol. 86, pp. 1110-1116, 2002).

The "urinary metabolite" or "urinary tumor marker" to be measured in the present invention refers to any of urinary metabolites listed in Table 2 below. Such urinary metabolites are less susceptible to enzymes, structurally more stable, and are more convenient as tumor markers, than substances in the blood. In addition, such urinary markers are very accessible also for cancer screening, because they are sampled from the urine, which can be easily collected even from children. The term "marker group" refers to a combination of urinary tumor markers.

The term "measuring" refers to determination of a relative abundance or absolute concentration of a target metabolite in a urine sample. The term "relative abundance" refers to the ratio of the measured intensity of the target metabolite to a reference material intentionally added. The "absolute concentration" is a value determined by a technique in which a calibration curve has been plotted using the same metabolite with the target metabolite, and the absolute concentration of the target metabolite is calculated using the measured intensity on the basis of the calibration curve, where the calibration curve indicates the relationship between the metabolite concentration and the metabolite measured intensity. As used herein, the term "measuring urinary tumor marker" refers to and includes both measurement of a metabolite as a urinary tumor marker, and measurement of a secondary substance of, or a derivative from, the metabolite. The "secondary substance" and "derivative" respectively refer to a substance secondarily produced from such a metabolite as a urinary tumor marker and a substance derived from the metabolite. Examples of the "secondary substance" and "derivative" include, but are not limited to, fragments of the metabolite, and modified metabolites.

Table 2 lists main urinary tumor markers for use in the present invention. Urinary metabolites from fifty-eight healthy children and seven neuroblastoma-affected children (of which one is affected with stage 4S neuroblastoma) were comprehensively analyzed, from which fifteen (15) metabolites that are critical for neuroblastoma detection were extracted. In Table 2, the column "Metabolite" presents names of metabolites whose structures have been identified by database research. In Table 2, the upper column "Group (A)" presents ten urinary tumor markers (Group (A) markers), which are present at a high level in a neuroblastoma other than stage 4S neuroblastoma; and the lower column "Group (B)" presents five urinary tumor markers (Group (B) markers), which are present at a high level both in stage 4S neuroblastoma and in a neuroblastoma other than stage 4S neuroblastoma.

In Table 2, the column "Mass" presents the mass as detected by the detection means given in the column "Analysis mode". The "LC/MS Neg" and "LC/MS Pos" in the column "Analysis mode" respectively represent "negative ion detection mode of a liquid chromatograph-mass spectrometer (LC/MS)" and "positive ion detection mode of a liquid chromatograph-mass spectrometer (LC/MS)". This table indicates one of the LC/MS positive ion detection mode and the LC/MS negative ion detection mode as the analysis mode. However, some apparatuses to be used can switch between the positive ion detection mode and the negative ion detection mode quickly, and in this case, both the positive ion detection mode and the negative ion detection mode are listed as the analysis mode.

The metabolites listed in Table 2 may be classified, as indicated in the column "Metabolic pathway" in Table 2, into those involved in tyrosine metabolism, those involved in methionine-cysteine-SAM metabolism (hereinafter also simply referred to as a "methionine-related metabolism"), those involved in corticosteroids, those involved in pterin metabolism, and those involved in isoleucine metabolism.

TABLE 2

Urinary Tumor Markers

| Metabolite | Metabolic pathway | Mass | Analysis mode |
|---|---|---|---|
| Group (A) | | | |
| 3-methoxytyramine sulfate | tyrosine metabolism | 246.04416 | LC/MS Neg |
| xanthopterin | pterin metabolism | 180.0516 | LC/MS Pos |
| vanillactate | tyrosine metabolism | 211.06119 | LC/MS Neg |
| 3,4-dihydroxyphenylacetate | tyrosine metabolism | 123.04515 | LC/MS Neg |
| cystathionine | methionine-related metabolism | 223.07471 | LC/MS Pos |
| cortisol 21-glucuronide | corticosteroid | 537.23413 | LC/MS Neg |
| 3,4-dihydroxyphenylacetate sulfate | tyrosine metabolism | 246.99179 | LC/MS Neg |
| cortisol | corticosteroid | 361.20204 | LC/MS Neg |
| 3-methoxytyrosine | tyrosine metabolism | 212.09174 | LC/MS Pos |
| 3-methoxytyramine | tyrosine metabolism | 168.10191 | LC/MS Pos |
| Group (B) | | | |
| vanillylmandelate(VMA) | tyrosine metabolism | 197.04555 | LC/MS Neg |
| homovanillate(HVA) | tyrosine metabolism | 181.05063 | LC/MS Neg |
| 2-hydroxy-3-methylvalerate | isoleucine metabolism | 131.07136 | LC/MS Neg |
| 3-methoxy-4-hydroxyphenylglycol | tyrosine metabolism | 167.07028 | LC/MS Pos |
| 3-(4-hydroxyphenyl)lactate | tyrosine metabolism | 181.05063 | LC/MS Neg |

In an embodiment, 3-methoxytyramine sulfate listed in Table 2 is measured as a Group (A) marker. Specifically, the measurement target is a compound found to have a mass of 246.04416 in the LC/MS negative ion detection mode.

In an embodiment, xanthopterin listed in Table 2 is measured as a Group (A) marker. Specifically, the measurement target is a compound found to have a mass of 180.0516 in the LC/MS positive ion detection mode.

In an embodiment, vanillactate listed in Table 2 is measured as a Group (A) marker. Specifically, the measurement target is a compound found to have a mass of 211.06119 in the LC/MS negative ion detection mode.

In an embodiment, 3,4-dihydroxyphenylacetate listed in Table 2 is measured as a Group (A) marker. Specifically, the measurement target is a compound found to have a mass of 123.04515 in the LC/MS negative ion detection mode.

In an embodiment, cystathionine listed in Table 2 is measured as a Group (A) marker. Specifically, the measurement target is a compound found to have a mass of 223.07471 in the LC/MS positive ion detection mode.

In an embodiment, cortisol 21-glucuronide listed in Table 2 is measured as a Group (A) marker. Specifically, the measurement target is a compound found to have a mass of 537.23413 in the LC/MS negative ion detection mode.

In an embodiment, 3,4-dihydroxyphenylacetate sulfate listed in Table 2 is measured as a Group (A) marker. Specifically, the measurement target is a compound found to have a mass of 246.99179 in the LC/MS negative ion detection mode.

In an embodiment, cortisol listed in Table 2 is measured as a Group (A) marker. Specifically, the measurement target is a compound found to have a mass of 361.20204 in the LC/MS negative ion detection mode.

In an embodiment, 3-methoxytyrosine listed in Table 2 is measured as a Group (A) marker. Specifically, the measurement target is a compound found to have a mass of 212.09174 in the LC/MS positive ion detection mode.

In an embodiment, 3-methoxytyramine listed in Table 2 is measured as a Group (A) marker. Specifically, the measurement target is a compound found to have a mass of 168.10191 in the LC/MS positive ion detection mode.

In an embodiment, vanillylmandelate (vanillylmandelic acid) (VMA) listed in Table 2 is measured as a Group (B) marker. Specifically, the measurement target is a compound found to have a mass of 197.04555 in the LC/MS negative ion detection mode.

In an embodiment, homovanillate (homovanillic acid) (HVA) listed in Table 2 is measured as a Group (B) marker. Specifically, the measurement target is a compound found to have a mass of 181.05063 in the LC/MS negative ion detection mode.

In an embodiment, 2-hydroxy-3-methylvalerate listed in Table 2 is measured as a Group (B) marker. Specifically, the measurement target is a compound found to have a mass of 131.07136 in the LC/MS negative ion detection mode.

In an embodiment, 3-methoxy-4-hydroxyphenylglycol listed in Table 2 is measured as a Group (B) marker. Specifically, the measurement target is a compound found to have a mass of 167.07028 in the LC/MS positive ion detection mode.

In an embodiment, 3-(4-hydroxyphenyl)lactate listed in Table 2 is measured as a Group (B) marker. Specifically, the measurement target is a compound found to have a mass of 181.05063 in the LC/MS negative ion detection mode.

The mass spectrometer used in the analyses of the metabolites listed in Table 2 has a very high resolution and enables measurement of the mass down to the second, third, fourth, or approximately fifth decimal place. A mass spectrometer having a low resolution, when used, measures the mass as integers or digits in the first decimal place.

According to the present invention, neuroblastoma detection and therapeutic effect monitoring may be conducted by using, of the urinary tumor markers listed in Table 2, at least one Group (A) marker, where necessary in combination with at least one Group (B) marker.

Group (A): 3-methoxytyramine sulfate, xanthopterin, vanillactate, 3,4-dihydroxyphenyl acetate, cystathionine, cortisol 21-glucuronide, 3,4-dihydroxyphenylacetate sulfate, cortisol, 3-methoxytyrosine, and 3-methoxytyramine Group (B): 2-hydroxy-3-methylvalerate, vanillylmandelate (VMA), homovanillate (HVA), 3-methoxy-4-hydroxyphenyl glycol, and 3-(4-hydroxyphenyl)lactate.

According to the present invention, neuroblastoma detection and therapeutic effect monitoring with still higher accuracy and precision can be conducted by using at least two, or three or more urinary tumor markers. For example, of the urinary tumor markers listed in Table 2, two or more Group (A) markers and/or two or more Group (B) markers may be used in combination. The combination of markers is not particularly limited.

In a preferred embodiment, urinary tumor markers involved in different metabolic pathways may be used in combination. For example, of the Group (A) markers, preferred may be the combination of markers belonging to different Subgroups selected from the following Subgroups (A-1) to (A-4):

(A-1): at least one selected from 3-methoxytyramine sulfate, vanillactate, 3,4-dihydroxyphenylacetate, 3,4-dihydroxyphenylacetate sulfate, 3-methoxytyrosine, and 3-methoxytyramine, each of which is involved in tyrosine metabolism;

(A-2): xanthopterin involved in pterin metabolism;

(A-3): cystathionine involved in methionine-related metabolism; and (A-4): at least one selected from cortisol 21-glucuronide and cortisol, which are corticosteroids.

Of the Group (B) markers, preferred may be the combination of a marker belonging to Subgroup (B-1) with a marker belonging to Subgroup (B-2):

(B-1): 2-hydroxy-3-methylvalerate involved in isoleucine metabolism; and (B-2): at least one selected from vanillylmandelate (VMA), homovanillate (HVA), 3-methoxy-4-hydroxyphenyl glycol, and 3-(4-hydroxyphenyl)lactate, each of which is involved in tyrosine metabolism.

In a more preferred embodiment, at least three different Group (A) urinary tumor markers may be measured. For example, markers of Subgroups (A-1), (A-2), and (A-3) in combination, markers of Subgroups (A-1), (A-2), and (A-4) in combination, markers of Subgroups (A-2), (A-3), and (A-4) in combination, or markers of Subgroups (A-1), (A-3), and (A-4) in combination may be measured. In a specific embodiment, measurement can be performed on the combination of 3-methoxytyramine sulfate belonging to Subgroup (A-1), xanthopterin belonging to Subgroup (A-2), and cortisol belonging to Subgroup (A-4).

In another preferred embodiment, at least three of the Group (B) urinary tumor markers may be measured. For example, one Subgroup (B-1) marker and two Subgroup (B-2) markers may be measured in combination. In a specific embodiment, measurement can be performed on 2-hydroxy-3-methylvalerate belonging to Subgroup (B-1), and VMA and HVA belonging to Subgroup (B-2) in combination.

Each of the urinary tumor markers listed in Table 2, when used alone, can be used to detect neuroblastoma. Preferably, the marker or markers to be used may include 2-hydroxy-3-methylvalerate as a Group (B) marker. Also preferably, the markers to be used may include 3-methoxytyramine sulfate as a Group (A) marker.

A urinary tumor marker, when analyzed alone, has only to be compared and analyzed one by another. However, two or more different urinary tumor markers, when to be evaluated, may require very complicated comparison and analysis, because there are a wide variety of combinations of markers. To eliminate or minimize the complexity, one can employ evaluation variables mentioned below, i.e., a precision variable R2Y and a predictor variable Q2, as criteria for selecting a good combination among combinations of markers.

$$R2Y = 1 - \frac{\Sigma(Yobs - Ycalc)^2}{\Sigma(Yobs - \overline{Y})^2}$$

$$Q2 = 1 - \frac{\Sigma(Yobs - Ypred)^2}{\Sigma(Yobs - \overline{Y})^2}$$

In the expressions, Yobs represents the measured value; Ycalc represents the value calculated by OPLS; Ypred represents the predicted value determined by cross-validation; and $\overline{Y}$ represents the average. The "cross-validation" refers to a technique by which data are divided, a part of the divided data is initially analyzed, the remainder is used to test or evaluate the analysis and to thereby verify and check the validity of the analysis itself. The expressions indicate that the model has higher precision with a precision variable R2Y approaching 1, and the model has higher predictability with a predictor variable Q2 approaching 1. The combination use of markers with high precision variables and high predictor variables, when used in neuroblastoma detection, probably enables detection with higher precision.

The combination of urinary tumor markers may be selected appropriately according typically to the type, sex, and age of the subject; the intended use such as neuroblastoma detection or therapy monitoring; and others.

Figure 2:
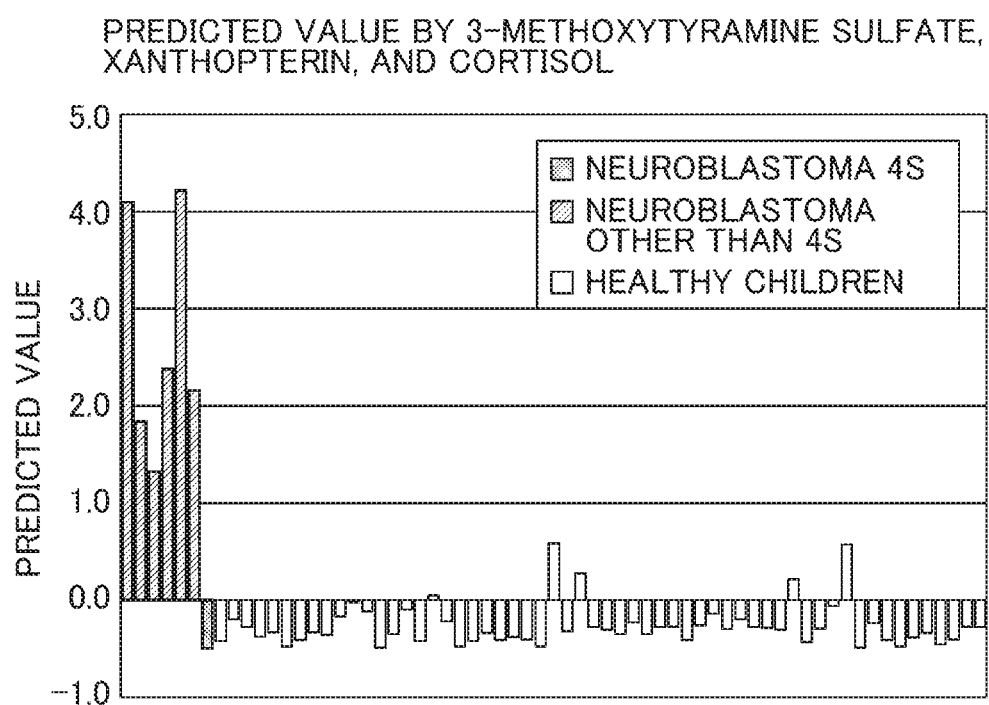
FIG. 2 is a graph indicating predicted values when a combination of markers specific to neuroblastoma other than stage 4S (3-methoxytyramine sulfate, xanthopterin, and cortisol) is applied to a cancer examination model.
Figure 3:
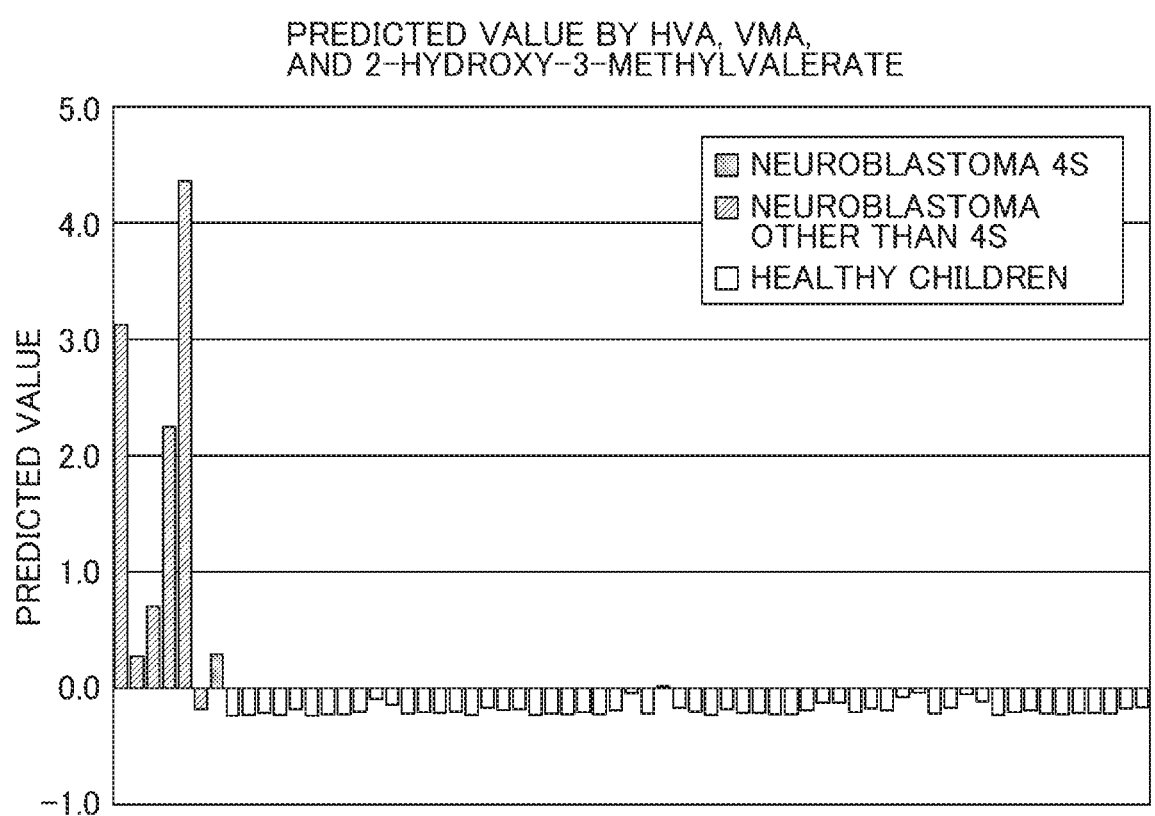
FIG. 3 is a graph indicating predicted values when a combination of markers that are detected in neuroblastoma in any of stages including stage 4S (HVA, VMA, and 2-hydroxy-3-methylvalerate) is applied to a cancer examination model.
Figure 4:
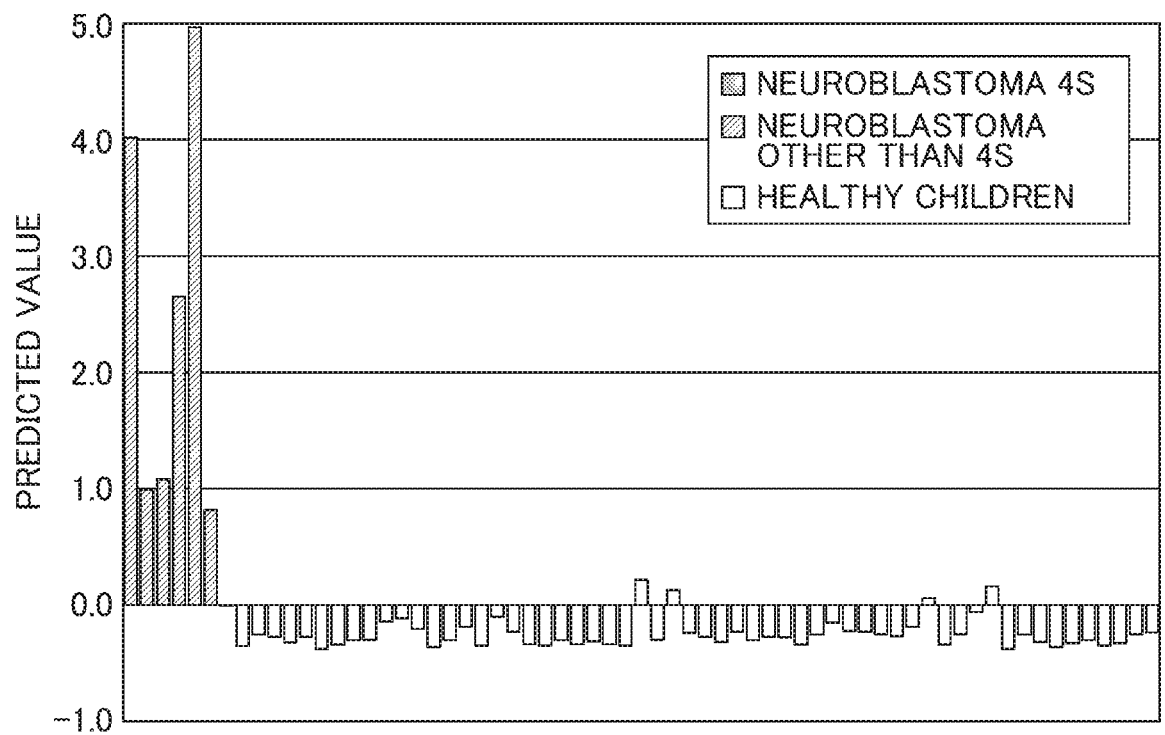
FIG. 4 is a referential graph indicating predicted values when the total of six markers including the markers specific to neuroblastoma other than stage 4S and the markers detected in neuroblastoma in any of stages including stage 4S are applied to a cancer examination model.

Urinary tumor markers may be distinguished or identified typically by a partial least square method, which is a kind of multivariate analyses, and particularly by orthogonal partial least square-discriminant analysis (OPLS-DA). Assume that a multivariate analysis is performed using, in combination, different metabolites that vary in subjects with neuroblastoma as compared with healthy subjects. In this case, when a multidimensional data is used as intact, the features of the data may be elusive. To eliminate or minimize this, such a multidimensional data preferably contracts to a two-dimensional or three-dimensional data and is visualized. For example, FIGS. 2 to 4 illustrate exemplary analytical data as plotted. A principal component analysis or another analysis technique known in the art can be employed as the multivariate analysis.

The "urine sample" refers to urine collected from the subject, and a sample obtained by treating the urine, such as urine treated with a preservative such as toluene, xylene, or hydrochloric acid.

The subject may be a child, specifically, a child aged 0 to 15 years. Preferably, the subject may be a child (infant) under 12 months of age, because stage 4S neuroblastoma is often observed in such children. However, the subject may not be limited to humans, but may be any of other mammals exemplified typically by primates (such as monkeys and chimpanzees), livestock (such as cattle, horses, pigs, and sheep), pet animals (such as dogs and cats), and laboratory animals (such as mice, rats, and rabbits).

The measurement of a urinary tumor marker means measurement of the amount or concentration of the marker in a urine sample preferably semi-quantitatively or quantitatively. The "amount" of the marker may be an absolute amount or a relative amount. The measurement can be performed directly or indirectly. The "direct measurement" may include measurement of the amount or concentration of a target urinary metabolite on the basis of a signal that correlates directly with the number of molecules of the target in the sample. The signal as above may typically be based on a specific physical or chemical property of the urinary metabolite. The indirect measurement may be measurement of a signal derived from a secondary component (specifically, a component other than the urinary metabolite). Non-limiting examples of the secondary component may include ligands, labels, and enzymatic reaction products.

In an embodiment of the present invention, the measurement target may be a urinary tumor marker, specifically, a urinary metabolite. The measurement may be performed by any technique or with any means (device) known in the art. For example, the urinary tumor marker can be measured with a measuring device that measures a physical or chemical property specific to the target urinary metabolite, such as a device that accurately measures the molecular weight or NMR spectrum of the metabolite. Non-limiting examples of the device for measuring the urinary metabolite may include analyzers such as mass spectrometers, NMR analyzers, two-dimensional electrophoresis apparatuses, chromatographs, and liquid chromatograph-mass spectrometers (LC/MS). The urinary tumor marker may be measured with each of different analyzers alone or in combination.

Alternatively, the urinary metabolite can be measured using a reagent for detecting a metabolite to be measured when the reagent is applicable. Non-limiting examples of the reagent may include immunoreaction reagents and enzymatic reaction reagents.

The urinary metabolites listed in Table 2 can be measured using LC/MS, since they have been found or identified using LC/MS.

As described above, a urinary tumor marker may be measured in a urine sample collected from a subject, and, on the basis of the result, a neuroblastoma may be detected in the subject. In addition, the urinary tumor marker may be measured in urine samples collected from the subject at different points of time.

The neuroblastoma detection method according to the present invention can determine the presence and progression of a neuroblastoma in an early stage. In particular, the method can distinguish stage 4S neuroblastoma, which has a good prognosis, from neuroblastoma in other stages and contributes to detailed determination of strategies of examination and therapy. A simple examination, when enabling determination whether the subject is affected with stage 4S neuroblastoma, is expected to eliminate or minimize an invasion risk caused not only by therapy, but also by examination. The method allows the subject to undergo a neuroblastoma therapy early and to undergo a therapy suitable typically for a specific malignancy. The method enables monitoring of a therapeutic effect on neuroblastoma and enables consideration whether the therapy is to be discontinued, or continued, or changed according to the monitored therapeutic effect. In addition, the method employs a urine sample, is therefore minimally invasive, enables simple and inexpensive evaluation of neuroblastoma, and is significantly advantageous particularly for children, whose periodical blood sampling is difficult.

The neuroblastoma detection method according to the present invention can be easily and simply performed using a kit and/or apparatus which includes a means for measuring a urinary tumor marker which is a urinary metabolite.

The neuroblastoma detection kit according to the present invention includes a means for measuring, in a urine sample, at least one Group (A) marker, of the urinary tumor markers listed in Table 2; and a means for measuring, in the urine sample, at least one Group (B) marker.

A non-limiting example of the kit according to the present invention may be a mass spectrometry reagent set, which typically includes components such as an isotope labeling reagent, a fractionating mini-column, and a buffer. Another non-limiting example of the kit may be an immunoreaction reagent set, which typically includes components such as a primary antibody-immobilized substrate, and a secondary antibody. A still another example may be an enzymatic reaction reagent set, which typically includes components such as an enzyme and a buffer. The kit according to the present invention may include any of other components such as an instruction manual giving a procedure and protocol for performing the method according to the present invention, and a table indicating reference levels or reference level ranges for use in neuroblastoma detection.

Such components contained in the kit according to the present invention may be provided individually, or together in a single container. Preferably, the kit according to the present invention may include all components necessary for performing the method according to the present invention typically as components in adjusted concentrations. This may be preferred for ready to use.

The neuroblastoma detection apparatus according to the present invention may include:

a measuring unit which is configured to measure, of the urinary tumor markers listed in Table 2, at least one Group (A) marker and at least one Group (B) marker in a urine sample;

a comparing unit which is configured to compare the measured values of the urinary tumor markers measured in the measuring unit with corresponding reference levels or previous measured values; and a determining unit which is configured to detect a neuroblastoma on the basis of the comparison results obtained in the comparing unit.

The neuroblastoma detection apparatus according to the present invention, when employing a multivariate analysis, may include:

a measuring unit which is configured to measure, of the urinary tumor markers listed in Table 2, at least one Group (A) marker and at least one Group (B) marker in a urine sample;

a comparing unit which is configured to compare a first calculated value with a reference level or a second calculated value, where the first calculated value results from multivariate analysis of the explanatory variables measured in the measuring unit (the amounts or concentrations of the urinary tumor markers, or the observed ionic strength ratios of urinary tumor markers that increase or decrease in neuroblastoma patients as compared with healthy children), where the reference level is a calculated objective variable calculated on the basis of a cancer examination model resulting from multivariate analysis of accumulated data and is an index indicating whether the subject is healthy or affected with a neuroblastoma and whether the neuroblastoma is stage 4S neuroblastoma, and where the second calculated value is a calculated objective variable previously obtained; and a determining unit which is configured to detect a neuroblastoma on the basis of the comparison result obtained in the comparing unit.

Figure 5:
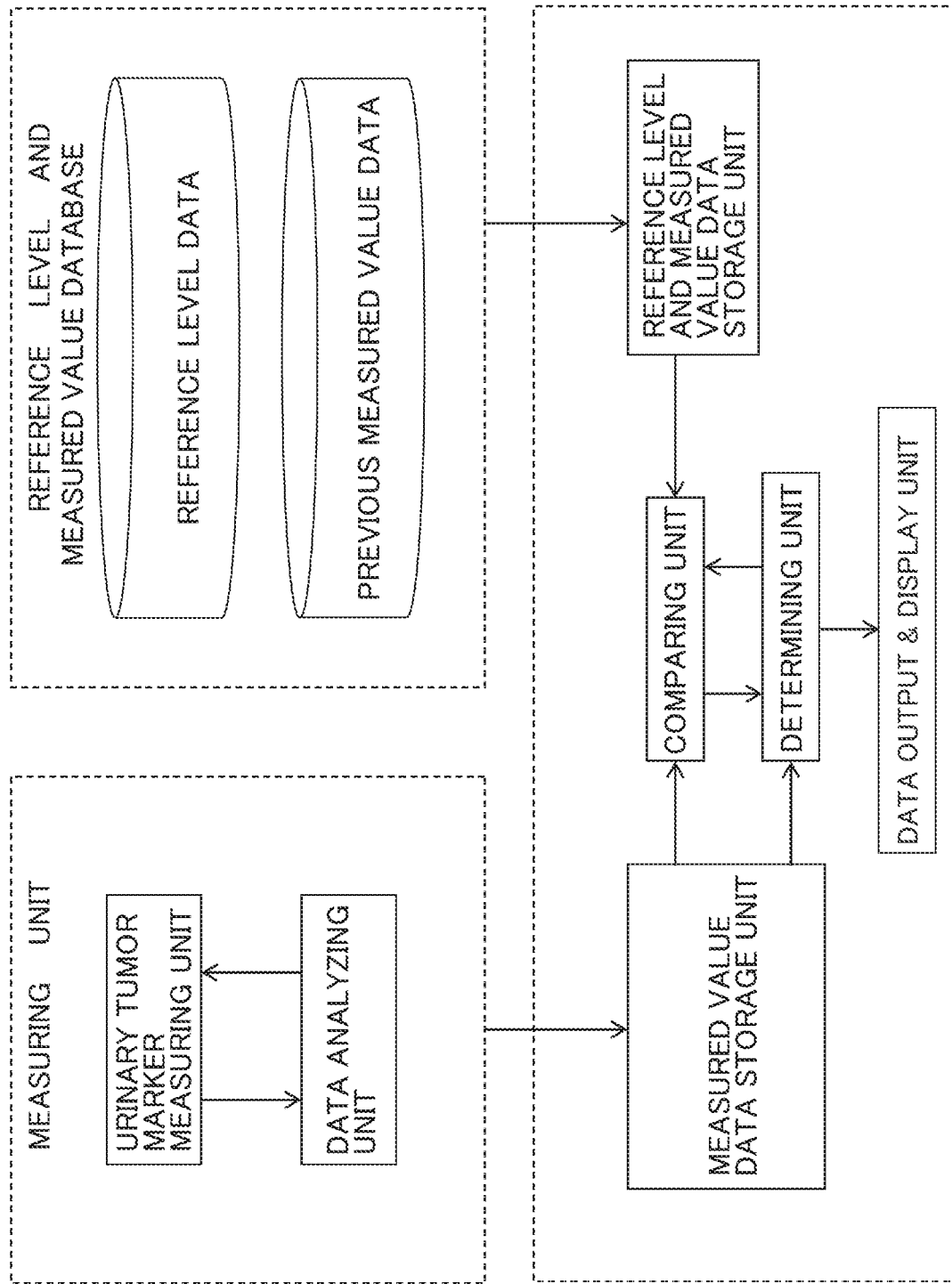
FIG. 5 depicts an exemplary configuration of an apparatus to which the present invention is applied.

The apparatus according to the present invention may preferably be a system including the measuring unit, the comparing unit, and the determining unit operably coupled to one another, to be able to perform the method according to the present invention. FIG. 5 illustrates an apparatus according to an embodiment of the present invention.

In the apparatus, the measuring unit may include a means for measuring urinary tumor markers in a urine sample, as described above, and typically has an analyzer such as a mass spectrometer, an NMR analyzer, a two-dimensional electrophoresis apparatus, a chromatograph, or a liquid chromatograph-mass spectrometer (LC/MS).

The measuring unit may include a data analyzer including software and a computer which is configured to process the measured values obtained typically from the analyzer as described above. The data analyzer is configured to calculate the amounts or concentrations of the urinary tumor markers contained in the urine sample by referring to data such as a calibration curve on the basis of the measured values obtained typically from the analyzer as described above. The data analyzer, when employing multivariate analysis, is configured to calculate an objective variable on the basis of a cancer examination model, where the cancer examination model results from multivariate analysis of the explanatory variables measured in the measuring unit (the amounts or concentrations of the urinary tumor markers, or the observed ionic strength ratios of urinary tumor markers that increase or decrease in neuroblastoma patients as compared with healthy children), and where the calculated value may serve as an index indicating whether the subject is healthy or affected with a neuroblastoma, and whether the neuroblastoma is stage 4S neuroblastoma. The data analyzer can include components such as a signal indicator, a unit that analyzes the measured values, and a computer unit.

The comparing unit may be configured to read out reference levels relating to the amounts or concentrations of the urinary tumor markers typically from a storage device (database), and to compare the reference levels with the measured values of the urinary tumor markers measured in the measuring unit. The comparing unit, when employing multivariate analysis, may be configured to read out the reference level of the objective variable typically from a storage device (database), and to compare the reference level with the calculated objective variable obtained in the measuring unit. In this process, the comparing unit may be configured to selectively read out appropriate reference levels corresponding to the types of the urinary tumor markers. Alternatively, in serial monitoring in the same subject, the comparing unit may be configured to read out the previous measured values typically from a storage device (database) and to compare the previous measured values with the measured values of the urinary tumor markers measured in the measuring unit.

The determining unit may be configured to detect a neuroblastoma on the basis of the results of comparisons between the measured values and the reference levels for the urinary tumor markers in the comparing unit, or on the basis of the comparisons among measured values of the urinary tumor markers measured at different points of time in the comparing unit. The determining unit, when employing multivariate analysis, may be configured to detect a neuroblastoma on the basis of the comparison results between calculated objective variables and the reference level in the comparing unit, or on the basis of the comparison results of the calculated objective variables calculated at different points of time in the comparing unit. In this process, the determining unit may obtain information indicating, for example, the presence of a neuroblastoma and the stage of the neuroblastoma in the subject. A preferred apparatus may be one usable without knowledge of an expert clinician, and a non-limiting example thereof may be an electronic apparatus operable simply with the application of a sample.

The apparatus according to the present invention may further include any of other components such as a data storage unit and a data output-display unit.

As used herein, the term "neuroblastoma detection" refers to and encompasses not only detection of the presence of a neuroblastoma in a subject, but also prediction of the neuroblastoma risk in the subject, determination of the neuroblastoma stage in the subject, determination of the neuroblastoma prognosis in the subject, monitoring of the therapeutic effect on the neuroblastoma present in the subject, and assistance of neuroblastoma diagnosis. A therapy to be applied may vary depending on the neuroblastoma malignancy, exemplified by the stage and prognosis (such as metastasis and recurrence). This places an importance on determination of the neuroblastoma stage and prognosis. In particular, according to the present invention, whether a neuroblastoma is present, and whether the neuroblastoma is in stage 4S may be detected. As used herein, the concept "detection" also encompasses consecutive monitoring of an already detected or diagnosed neuroblastoma, and verification of such already performed neuroblastoma detection or diagnosis.

The "detection" with or by the neuroblastoma detection method, detection kit, and detection apparatus according to the present invention is intended to detect subjects in a statistically significant proportion. The "detection" with or by the neuroblastoma detection method, detection kit, and detection apparatus according to the present invention may also include the case where all the subjects (namely, 100% of the subjects) do not always gain correct results. The statistically significant proportion can be determined using any of a variety of known statistical evaluation tools, such as determination of a confidence interval, determination of a p-value, Student's t-test, and Mann-Whitney test. The confidence interval may preferably be at least 90%. The p-value may preferably be 0.1, 0.01, 0.05, 0.005, or 0.0001. More preferably, the neuroblastoma detection method, detection kit, and detection apparatus according to the present invention can appropriately detect a neuroblastoma among at least 60%, at least 80%, or at least 90% of subjects.

A specific, but non-limiting example of the neuroblastoma detection is as follows. In an embodiment, a urinary tumor marker may be measured in a urine sample from a subject, and the measured value may be compared with a reference level. When two or more urinary tumor markers are measured, the individual measured values of the urinary tumor markers may be compared with corresponding reference levels. Alternatively, it may also be acceptable that the measured values undergo multivariate analysis to give a calculated objective variable, and the calculated objective variable may be compared with a corresponding reference level.

The reference (reference level) may serve, in the case of the Group (A) markers, as an index for the presence of a neuroblastoma other than stage 4S neuroblastoma and may be the amount or concentration of the target urinary tumor marker, or the range of the amount or concentration; and, in the case of the Group (B) markers, may serve as an index for the presence of stage 4S neuroblastoma and may be the amount or concentration of the target urinary tumor marker, or the range of the amount or concentration. In contrast, when multivariate analysis is employed, the reference level may be a calculated objective variable that distinguishes healthy children from neuroblastoma patients, or distinguishes healthy children from stage 4S neuroblastoma patients. For example, the reference level can be derived from healthy children (population) or neuroblastoma low-risk children (population). Alternatively, the reference level can be derived from patients (patient population) such as patients with stage 4S neuroblastoma, or patients with a neuroblastoma other than stage 4S neuroblastoma, or a patients with a neuroblastoma having a specific prognosis. The reference level to be applied to each subject may vary depending on various physiological parameters such as the species, age, and sex of the subject animal.

Preferably, a database may be made to record the correlation of the amount or concentration of each urinary tumor marker with the presence of stage 4S neuroblastoma, or the presence of a neuroblastoma other than stage 4S neuroblastoma, or the specific prognosis. Then, the measured value of the target urinary tumor marker in the urine sample can be compared with the reference level in the database. The database as above may be useful as a reference level or reference level range each of which serves as an index indicating whether a neuroblastoma is present, or whether the neuroblastoma is in stage 4S, or serves as an index for prognosis.

Of the urinary tumor markers listed in Table 2, the Group (A) markers differ in their amount or concentration between patients with a neuroblastoma other than stage 4S neuroblastoma and healthy children and vary in their amount or concentration depending on the presence of a neuroblastoma, and between before and after the start of therapy. Specifically, the Group (A) markers listed in Table 2 increase in their amount or concentration in patients with a neuroblastoma other than stage 4S neuroblastoma, as compared with healthy children. A subject, when having a measured value of such a Group (A) marker higher than a reference level derived from the healthy children population or equal to or higher than a reference level derived from the neuroblastoma patient population, is considered to be affected with a neuroblastoma other than stage 4S neuroblastoma or to have a high risk of the affection.

Of the urinary tumor markers listed in Table 2, the Group (B) markers differ in their amount or concentration between neuroblastoma patients in any of stages including stage 4S and healthy children and vary in their amount or concentration by the presence of a neuroblastoma (in any of stages including stage 4S). Specifically, the Group (B) markers listed in Table 2 increase in their amount or concentration in neuroblastoma patients in any of stages including stage 4S, as compared with healthy children. A subject, when having a measured Group (B) marker level higher than a reference level derived from the healthy children population or equal to or higher than a reference level derived from the neuroblastoma (in particular, stage 4S) patient population, is considered to be affected with a neuroblastoma (in particular, stage 4S neuroblastoma) or to have a high risk of the affection.

Table 3 presents specific examples to detect a neuroblastoma using the urinary tumor markers listed in Table 2.

TABLE 3

| Case | Group (A) marker | Group (B) marker | Detection example |
|---|---|---|---|
| 1 | higher than reference level | higher than reference level | positive for neuroblastoma other than stage 4S |

TABLE 3-continued

| Case | Group (A) marker | Group (B) marker | Detection example |
|---|---|---|---|
| 2 | higher than reference level | lower than reference level | positive for neuroblastoma other than stage 4S |
| 3 | lower than reference level | higher than reference level | positive for neuroblastoma stage 4S |
| 4 | lower than reference level | lower than reference level | negative for neuroblastoma |

As shown in Table 3, a subject, when having a Group (A) marker level higher than the reference level (Cases 1 and 2), may be determined to be positive for neuroblastoma, and to be in a stage other than stage 4S. A subject, when having a Group (A) marker level lower than the reference level and a Group (B) marker level higher than the reference level (Case 3), may be determined to be positive for neuroblastoma and to be in stage 4S. A subject, when having a Group (A) marker level lower than the reference level and a Group (B) marker level lower than the reference level (Case 4), may be determined to be negative for neuroblastoma.

FIG. 1 depicts an exemplary flow chart of neuroblastoma detection using urinary tumor markers, to which the present invention is applied. According to the detection flow chart, urinary tumor markers in a urine sample may be measured. A subject, when having a high (+) predicted value for a urinary tumor marker that is present at a high level in neuroblastoma cases other than stage 4S (namely, Group (A) marker), may be determined to be positive for neuroblastoma and to be affected with a neuroblastoma other than stage 4S neuroblastoma. A subject, when having a low (−) Group (A) marker level, but having a high (+) predicted value for a urinary tumor marker that is present at a high value in cases with stage 4S neuroblastoma (namely, Group (B) marker), may be determined to be positive for neuroblastoma and to be in stage 4S. A subject, when having low levels of the both urinary tumor markers, may be determined to be negative for neuroblastoma.

In another embodiment, urine samples may be collected from a subject at different points of time, urinary tumor markers contained in the urine samples at the individual points of time may be measured, and the measured values of the urinary tumor markers may be compared between the individual points of time in measurement. More specifically, the amount or concentration (a) of a target urinary tumor marker at a first point of time may be compared with the amount or concentration (b) of the urinary tumor marker at a second point of time. When data undergoes multivariate analysis, a calculated value of one component at the first point of time may be compared with a calculated value of the component at the second point of time. The measurement may be performed sequentially at least two times, or 3, 4, 5, 10, 15, 20, 30, or more times, at intervals typically of 1 day, 2 days, 5 days, 1 week, 2 weeks, 3 weeks, 1 month, 2 months, 3 months, 6 months, 1 year, 2 years, 3 years, 5 years, or longer. The comparison as above may enable sequential monitoring and evaluation of a condition such as progression (advance), metastasis, or recurrence of neuroblastoma.

In still another embodiment, the urinary tumor markers for use in the present invention may be used to monitor the efficacy of a therapy (therapeutic agent or therapy) on neuroblastoma in a subject. Specifically, this method includes the steps as follows:

(a) measuring a urinary tumor marker or markers in a urine sample collected from a patient with neuroblastoma, before a treatment with or by the therapeutic agent or therapy;

(b) measuring the urinary tumor marker or markers in a urine sample collected from the patient with neuroblastoma, after the treatment with or by the therapeutic agent or therapy;

(c) repeating the step (b) as needed; and (d) monitoring the efficacy of the therapeutic agent or therapy on neuroblastoma, on the basis of the measurement results in the steps (a) to (c).

In the above method, a urine sample may be collected from a patient with neuroblastoma before the treatment with or by the therapeutic agent or therapy, and a urinary tumor marker or markers may be measured in the urine sample. Next, the patient with neuroblastoma may undergo the treatment with or by the therapeutic agent or therapy, from which another urine sample may be collected at an appropriate time, and the urinary tumor marker or markers may be measured in the urine sample. For example, the urine sample may be collected after the treatment immediately, 30 minutes later, 1 hour later, 3 hours later, 5 hours later, 10 hours later, 15 hours later, 20 hours later, 24 hours (1 day) later, 2 to 10 days later, 10 to 20 days later, 20 to 30 days later, and/or 1 month to 6 months later. The urinary tumor marker or markers in the urine sample can be measured as above. The measurement of the urinary tumor marker(s) before and after the therapy may enable monitoring of the efficacy of the treatment with or by the therapeutic agent or therapy. The monitoring results may contribute to consideration whether the therapy is to be discontinued, continued, or changed.

In addition, the neuroblastoma detection method may combine with a conventionally known neuroblastoma diagnosis method. Non-limiting examples of such known neuroblastoma diagnosis methods may include imaging examinations such as ultrasonography, computed tomography (CT), X-ray examination, magnetic resonance imaging (MRI), computed positron emission tomography (PET); endoscopy; bioptic pathologic examinations, such as bone marrow aspirate examination; and measurement of blood tumor markers.

On the basis of the evaluation results, a doctor can diagnose neuroblastoma of the subject and preform an appropriate treatment. Specifically, the present invention also relates to a method for detecting and treating a neuroblastoma in a subject. For example, a neuroblastoma may be detected in the subject in accordance with the neuroblastoma detection method according to the present invention. The subject, when evaluated as highly possibly having a developed neuroblastoma other than stage 4S neuroblastoma, may undergo a treatment for treating the neuroblastoma or for preventing neuroblastoma progression. When the subject is evaluated as having a neuroblastoma in an advanced stage or having a neuroblastoma with a poor prognosis, the therapy may be continued, or considered to be changed according to necessity. When the subject is evaluated as highly possibly having a developed stage 4S neuroblastoma, the target urinary tumor marker may be sequentially measured to monitor the neuroblastoma, so as to avoid excessive examination and therapy. The subject, when evaluated as highly possibly having a neuroblastoma, may undergo any other neuroblastoma diagnosis method as described above, to determine the presence of the neuroblastoma. In addition, on the basis of evaluation results before and after the therapy, the therapeutic effect may be monitored, to determine whether the therapy is to be discontinued, continued, or changed.

The neuroblastoma can be treated by each of different therapies, such as surgery, radiotherapy, chemotherapy, immunotherapy, proton beam therapy, and heavy ion radiotherapy, alone or in appropriate combination. A person skilled in the art can appropriately select such a neuroblastoma therapy in consideration typically of the type, stage, and malignancy of the neuroblastoma; and the sex, age, condition, and responsivity to the therapy, of the affected child.

An exemplary cancer examination in an examination center, to which the present invention is applied, will be illustrated below. The examination center may guide an examinee to the cancer examination corresponding typically to the request from the examinee. The examinee may select the number of biomarkers to be examined upon application of a primary examination. For example, the examinee may select one to three different urinary tumor markers as the biomarkers. Such urinary tumor markers may be used in combination with one or more other biomarkers as comprehensive cancer examination (analyses of various cancers at once).

Next, the examination center may give an examination kit necessary for the collection of urine to the examinee, typically by mail as needed. After receiving the examination kit, the examinee may typically give or deliver a specimen to the examination center. The examination center may cryopreserve the specimen at about −80° C., as needed for a subsequent examination. The examination center may perform a primary examination and send the examination result to the examinee.

The examinee may receive the primary examination result and, according to the result, may apply for a secondary examination or undergo a more detailed diagnosis. This may enable validation of suspected neuroblastoma in the primary examination and, in addition, enable identification of the neuroblastoma stage.

In an embodiment, according to the present invention, evaluation for the efficacy of a neuroblastoma therapy (therapeutic agent or therapy) or screening of neuroblastoma therapeutic agent candidates may also be conducted by using the urinary tumor markers for use in the present invention. Specifically, the method for evaluating the efficacy of a neuroblastoma therapy, and the method for screening a neuroblastoma therapeutic agent candidate may include the steps of:

(a) measuring a urinary tumor marker in a urine sample from an animal with a neuroblastoma which has undergone a treatment with a test therapeutic agent or therapy; and (b) evaluating the test therapeutic agent or therapy for efficacy on the neuroblastoma.

According to each method of the present invention, a urine sample may be collected from an animal with a neuroblastoma, specifically, an animal with neuroblastoma development or with a chance of neuroblastoma development, and a urinary tumor marker may be measured in the urine sample. Preferably, a urine sample may be collected from the animal with a neuroblastoma before a treatment with or by the test therapeutic agent or therapy and a urinary tumor marker may be measured in the urine sample. Then, the animal with a neuroblastoma may undergo a treatment with or by the test therapeutic agent or therapy, from which a urine sample at an appropriate point of time is collected, and the urinary tumor marker in the urine sample is measured. For example, the urine sample may be collected after the treatment immediately, 30 minutes later, 1 hour later, 3 hours later, 5 hours later, 10 hours later, 15 hours later, 20 hours later, 24 hours (1 day) later, 2 to 10 days later, 10 to 20 days later, 20 to 30 days later, and/or 1 month to 6 months later. The urinary tumor marker measurement in the urine sample and the neuroblastoma detection can be performed as above.

The subject animal may be a human affected with a neuroblastoma (preferably, a neuroblastoma in a specific stage), or a neuroblastoma model animal (such as a mouse, rat, or rabbit). In general, the efficacy of the test therapeutic agent or therapy may be verified in a model animal, and then may be evaluated in human typically by a clinical trial.

The type of test therapeutic agent or therapy as an evaluation or screening target may not be limited. Non-limiting examples of the test therapeutic agent or therapy may include any material factors, specifically, naturally-occurring molecules such as amino acids, peptides, oligopeptides, polypeptides, proteins, nucleic acids, lipids, carbohydrates (such as sugars), steroids, glycopeptides, glycoproteins, and proteoglycans; synthetic analogs or derivatives of naturally-occurring molecules, exemplified by peptide mimics and nucleic acid molecules (such as aptamers, antisense nucleic acids, and double-strand RNAs (RNAi)); non-natural molecules such as low-molecular organic compounds (such as inorganic and organic compound libraries, or combinatorial libraries); and mixtures of them. The therapeutic agent or therapy may be a single substance, or a complex including substances, or a foodstuff or a diet. Instead of the material factors, the test therapeutic agent or therapy may be, for example, any of radioactive rays and ultraviolet rays.

A person skilled in the art can easily determine the treatment of the animal with or by the test therapeutic agent or therapy, although the treatment may vary depending on the type of the therapeutic agent or therapy. For example, the person skilled in the art can appropriately determine the administration conditions such as dose, administration period, and administration route of the test therapeutic agent.

The efficacy of the test therapeutic agent or therapy can be considered for several conditions. Non-limiting examples of such conditions may include time or period, dose (large or small), and number of the treatment with or by the test therapeutic agent or therapy. For example, doses can be set typically by preparing a dilution series of the test therapeutic agent.

Therapeutic agents or therapies may combine with each other in testing, to consider the additive action and/or synergistic action of the test therapeutic agents or therapies.

The urinary tumor marker in the urine sample collected from the animal after the treatment with or by the test therapeutic agent or therapy may be measured, and the measured value may be compared with the amount or concentration before the treatment. This may enable the evaluation of the test therapeutic agent or therapy for the efficacy on neuroblastoma disappearance, neuroblastoma regression, neuroblastoma-associated symptom improvement, and discontinuation or retardation of neuroblastoma progression.

For example, the Group (A) markers listed in Table 2 are urinary tumor markers that increase in their amount or concentration in patients with a neuroblastoma other than stage 4S neuroblastoma, as compared with healthy children. Assume that the subject after the treatment has a Group (A) marker level lower than the level before the treatment. This indicates that the test therapeutic agent or therapy may be efficacious on neuroblastoma disappearance, neuroblastoma regression, neuroblastoma-associated symptom improvement, and/or discontinuation or retardation of neuroblastoma progression. In contrast, assume that the subject after the treatment has a Group (A) marker level that is higher than the level before the treatment or shows no significant difference from the level before the treatment. This indicates that the test therapeutic agent or therapy may not be efficacious on the neuroblastoma treatment.

For example, the Group (B) markers listed in Table 2 are urinary tumor markers that increase in their amount or concentration in patients with neuroblastoma in any of stages including stage 4S. Assume that the subject after the treatment has a Group (B) marker level lower than the level before the treatment. This indicates that the test therapeutic agent or therapy may be efficacious on disappearance, regression, neuroblastoma-associated symptom improvement, and/or discontinuation or retardation of progression of, a neuroblastoma in any of stages including stage 4S. In contrast, assume that the subject after the treatment has a Group (B) marker level that is higher than the level before the treatment or shows no significant difference from the level before the treatment. This indicates that the test therapeutic agent or therapy may not be efficacious on neuroblastoma therapy.

The method can employ a multivariate analysis using two or more of these urinary tumor markers. For example, two, three, four, five, or six different urinary tumor markers, when used, may give OPLS-DA analytical data as illustrated in FIGS. 2 to 4. FIGS. 2 to 4 demonstrate that the discrimination lines may enable distinguishing of healthy children from neuroblastoma patients (stage 4S or a stage other than stage 4S), where each discrimination line is, for example, a line at which the calculated value of a component indicated in the abscissa passes through zero (0). Specifically, assume that, in a new subject or target, the calculated value of the component indicated in the abscissa moves from the neuroblastoma patient region to the healthy children region. This demonstrates that the test therapeutic agent or therapy may be efficacious on neuroblastoma disappearance, neuroblastoma regression, neuroblastoma-associated symptom improvement, and/or discontinuation or retardation of neuroblastoma progression. In contrast, assume that the calculated value of the component indicated in the abscissa remains in the neuroblastoma patient region. This indicates that the test therapeutic agent or therapy may not be efficacious on neuroblastoma therapy.

As is described above, according to the method of the present invention for evaluating the efficacy of a neuroblastoma therapy, a therapeutic agent or therapy for treating or preventing a neuroblastoma, in particular, a neuroblastoma other than stage 4S neuroblastoma can be identified, or a therapeutic agent or therapy for treating or preventing stage 4S neuroblastoma can be identified, and the efficacy of the therapeutic agent or therapy can be verified.

The present invention will be illustrated in further detail with reference to several embodiments or examples below. It should be noted, however, that the examples are provided only for the sake of describing the present invention and are never construed to limit or restrict the scope of the invention as disclosed herein.

EXAMPLES

Example 1: Comprehensive Analysis of Neuroblastoma-Related Urinary Metabolites

To identify urinary tumor markers specific to neuroblastoma, a global analysis of urinary metabolites was performed on 58 healthy children and 7 neuroblastoma-affected children before therapy, in Nagoya University Graduate School of Medicine, Surgery, Pediatric Surgery Laboratory.

Specifically, metabolites in urine of neuroblastoma-affected children and in urine of healthy children of the same age were comprehensively analyzed using a liquid chromatograph-mass spectrometer (LC/MS) to specify metabolites that significantly increase or decrease in the childhood cancer-affected (neuroblastoma-affected) children as compared with the healthy children, to thereby find urinary tumor markers that can distinguish between healthy children and childhood cancer-affected children by multivariate analysis. As a result, urinary tumor markers that distinguish between the two groups were found (Japanese Patent Application No. 2018-055998, filed Mar. 23, 2018).

During the analysis process, one affected child diagnosed as stage 4S neuroblastoma differed in urinary metabolite profiles from six children affected with a neuroblastoma other than stage 4S neuroblastoma, as follows:

the one child had an apparently small number of types of urinary metabolites having a significant difference from those in the healthy children, as compared with the other affected children; and the one child had remarkably low metabolite levels, even with a significant difference, as compared with the other affected children, and had only one metabolite that is present at a remarkably high level as equivalent to the other affected children.

The stage 4S neuroblastoma is a special group that is observed in infants, regresses spontaneously without therapy, and has a good prognosis. Identification of the stage 4S group by a simple examination can avoid excessive examination and therapy. To meet this requirement, screening of urinary tumor markers that identify the stage 4S group was attempted. Specifically, top 30 urinary metabolites were selected from LC/MS measured values of urinary metabolites by random forests (RF), from which exogenous substances, compounds whose structure is unknown, and compounds that are present in low levels in neuroblastoma were excluded. The 95 percent confidence (data) interval of the healthy children group was compared with the corresponding data of the cancer-affected children (the LC/MS measured values underwent normal approximation by logarithmic transformation), the results of which are given in the table below.

TABLE 4

| | | | Significant difference from healthy children | |
| --- | --- | --- | --- | --- |
| RF rank | Metabolite | Metabolic pathway | Stage 4S | 6 cases with neuroblastoma other than stage 4S |
| 2 | vanillylmandelate (VMA) | tyrosine metabolism | high | high (5 cases) |
| 6 | homovanillate (HVA) | tyrosine metabolism | high | high (5 cases) |
| 7 | 3-methoxytyramine sulfate | tyrosine metabolism | no | high (6 cases) |

TABLE 4-continued

| | | | Significant difference from healthy children | |
|---|---|---|---|---|
| RF rank | Metabolite | Metabolic pathway | Stage 4S | 6 cases with neuroblastoma other than stage 4S |
| 11 | xanthopterin | pterin metabolism | no | high (5 cases) |
| 14 | vanillactate | tyrosine metabolism | no | high (5 cases) |
| 15 | 2-hydroxy-3-methylvalerate | isoleucine metabolism | [high] | high (3 cases) |
| 16 | 3,4-dihydroxyphenylacetate | tyrosine metabolism | no | high (5 cases) |
| 17 | cystathionine | methionine-related metabolism | no | high (4 cases) |
| 18 | cortisol 21-glucuronide | corticosteroid | no | high (4 cases) |
| 20 | 3,4-dihydroxyphenylacetate sulfate | tyrosine metabolism | no | high (5 cases) |
| 21 | cortisol | corticosteroid | no | high (4 cases) |
| 22 | 3-methoxytyrosine | tyrosine metabolism | no | high (5 cases) |
| 24 | 3-methoxy-4-hydroxyphenylglycol | tyrosine metabolism | high | high (4 cases) |
| 26 | 3-methoxytyramine | tyrosine metabolism | no | high (5 cases) |
| 28 | 3-(4-hydroxyphenyl)lactate | tyrosine metabolism | high | high (3 cases) |

The analytical data demonstrated that there are urinary tumor markers that do not take a high value in the stage 4S neuroblastoma. Accordingly, the combination of a urinary tumor marker whose level is high in a neuroblastoma other than stage 4S neuroblastoma (Group (A) marker) with a urinary tumor marker whose level is high in a neuroblastoma in any of stages including stage 4S (Group (B) marker) can assist in diagnosing whether a subject is affected with a neuroblastoma and in diagnosing whether the neuroblastoma is in stage 4S.

Example 2: Construction of Cancer Evaluation Model Using Group (A) Markers and Group (B) Markers On each of the Group (A) markers and the Group (B) markers selected in Example 1, prediction models were made by OPLS-DA on all combinations, and the performance indices (in particular, predictor variables) of the models were determined. In particular, combinations of urinary metabolites involved in different metabolisms were selected as marker candidates.

Specifically, to distinguish between healthy children and neuroblastoma-affected children, cancer examination models were determined by orthogonal projections to latent structures-discriminant analysis (OPLS-DA) using indices expressed as follows:

$$R2Y = 1 - \frac{\Sigma(Yobs - Ycalc)^2}{\Sigma(Yobs - \bar{Y})^2}$$

$$Q2 = 1 - \frac{\Sigma(Yobs - Ypred)^2}{\Sigma(Yobs - \bar{Y})^2}$$

In the expressions, Yobs represents the measured value; Ycalc represents the value calculated by OPLS; Ypred represents the predicted value according to cross-validation; and represents the average. The "cross-validation" refers to a technique by which data are divided, a part of the divided data is initially analyzed, and the remainder is used to test or evaluate the analysis and to verify and check the validity of the analysis. It is indicated that the model has higher precision with a precision variable R2Y approaching 1, and the model has higher predictability with a predictor variable Q2 approaching 1.

FIGS. 2 and 3 illustrate the results of prediction models having particularly high evaluation indices as defined above. FIG. 2 is a graph showing predicted values of a cancer examination model to which the combination of markers specific to neuroblastoma other than stage 4S neuroblastoma, namely, three Group (A) markers, i.e., 3-methoxytyramine sulfate (tyrosine metabolism), xanthopterin (pterin metabolism), and cortisol (corticosteroid), was applied. This model had an explanatory variable of 0.857 and a predictor variable of 0.804, and stage 4S neuroblastoma-affected children were classified as being negative for these markers.

FIG. 3 is a graph showing predicted values of a cancer examination model to which the combination of markers detectable in any of neuroblastoma including stage 4S neuroblastoma, namely, three Group (B) markers, i.e., HVA (tyrosine metabolism), VMA (tyrosine metabolism), and 2-hydroxy-3-methylvalerate (isoleucine metabolism), is applied. This model had an explanatory variable of 0.541 and a predictor variable of 0.415, and stage 4S neuroblastoma-affected children were classified as being positive for these markers.

As described above, a subject, when being negative for Group (A) markers (for example, FIG. 2) and being positive for Group (B) markers (for example, FIG. 3), can be said to be highly possibly affected with stage 4S neuroblastoma. In contrast, a subject, when being positive for Group (A) markers (for example, FIG. 2), can be said to be highly possibly affected with a neuroblastoma (in particular, a neuroblastoma in a stage other than stage 4S).

As illustrated in FIG. 3, one (Case No. 15) of the affected children with a neuroblastoma other than stage 4S neuroblastoma has high values for, of Group (A) markers, 3-methoxytyramine sulfate, cystathionine, cortisol 21-glucuronide, and cortisol, but was negative for all the Group (B) markers. It is reported that a neuroblastoma that is not high in Group (B) markers (in particular, HVA and VMA) has a low differentiation degree, and it is known that the levels of the Group (B) markers (in particular, HVA and VMA) inversely correlate with the amplification of the N-myc (MYCN) gene, which is known to be a poor prognostic factor (Nakagawara et al., Journal of The Japanese Society of Pediatric Surgeons, Vol. 23, Issue 2, p. 396). Accordingly, a subject, when being positive for Group (A) marker(s) and being negative for Group (B) marker(s), may possibly be associated with a poor neuroblastoma prognosis.

Of the healthy children, five children had a level of HVA or VMA, each of which is a Group (B) marker, higher than the 95 percent data interval, of which one had levels of both HVA and VMA higher than the 95 percent data interval. All the five children were infants under 12 months of age (of fifty-eight healthy children, ten children were infants under 12 months of age). In the other healthy children, of the top 30 urinary metabolites as determined by the random forests (RF) in Example 1, none or only one urinary metabolite level was out of the 95 percent data interval. In contrast, in the five infants under 12 months of age, the levels of three to seven urinary metabolites including HVA and VMA were out of the 95 percent data interval. The results demonstrate that half of the infants under 12 months of age are analogous in urinary metabolites to neuroblastoma, namely, were false-positive for neuroblastoma; and that urinary tumor marker examinations should be performed with setting reference levels corresponding to the age and/or with paying special attention to infants under 12 months of age.

Comparative Example

As a reference, FIG. 4 shows predicted values of a cancer examination model to which the combination of the three Group (A) markers and the three Group (B) markers, total six markers, is applied. This model had an explanatory variable of 0.705 and a predictor variable of 0.648. Stage 4S neuroblastoma-affected children are classified as being positive, but cannot be distinguished from subjects affected with a neuroblastoma other than stage 4S neuroblastoma.

The entire contents of all publications, patents, and patent applications cited in the description are incorporated herein by reference as they are.

The invention claimed is:
1. A method for detecting a neuroblastoma, the method comprising:
   measuring a urinary tumor marker in a urine sample derived from a subject, the step including:
   measuring at least one urinary tumor marker selected from Group (A) as follows:
   (A) 3-methoxytyramine sulfate, xanthopterin, vanillactate, 3,4-dihydroxyphenylacetate, cystathionine, cortisol 21-glucuronide, 3,4-dihydroxyphenylacetate sulfate, cortisol, 3-methoxytyrosine, and 3-methoxytyramine; and measuring at least one urinary tumor marker selected from Group (B) as follows:
   (B) 2-hydroxy-3-methylvalerate, vanillylmandelate, homovanillate, 3-methoxy-4-hydroxyphenyl glycol, and 3-(4-hydroxyphenyl)lactate; and
   detecting a neuroblastoma in the subject based on results of the measurement,
   wherein at least three of the Group (A) urinary tumor markers and at least one of the Group (B) urinary tumor markers are measured,
   wherein when the at least one Group (A) urinary tumor marker is at a level higher than a reference level, it is indicated that the subject is positive for a neuroblastoma and is in a stage other than stage 4S, and
   wherein when the at least one Group (A) urinary tumor marker is at a level lower than the reference level, but the at least one Group (B) urinary tumor marker is at a level higher than a reference level, it is indicated that the subject is positive for a neuroblastoma and is in stage 4S.
2. A method for detecting a neuroblastoma, the method comprising:
   measuring a urinary tumor marker in a urine sample derived from a subject, the step including:
   measuring at least one urinary tumor marker selected from Group (A) as follows:
   (A) 3-methoxytyramine sulfate, xanthopterin, vanillactate, 3,4-dihydroxyphenylacetate, cystathionine, cortisol 21-glucuronide, 3,4-dihydroxyphenylacetate sulfate, cortisol, 3-methoxytyrosine, and 3-methoxytyramine, and
   measuring at least one urinary tumor marker selected from Group (B) as follows:
   (B) 2-hydroxy-3-methylvalerate, vanillylmandelate, homovanillate, 3-methoxy-4-hydroxyphenyl glycol, and 3-(4-hydroxyphenyl)lactate, and
   detecting a neuroblastoma in the subject based on results of the measurement,
   wherein when the at least one Group (A) urinary tumor marker is at a level higher than a reference level, it is indicated that the subject is positive for a neuroblastoma and is in a stage other than stage 4S, and
   wherein when the at least one Group (A) urinary tumor marker is at a level lower than the reference level, but the at least one Group (B) urinary tumor marker is at a level higher than a reference level, it is indicated that the subject is positive for a neuroblastoma and is in stage 4S,
   wherein the Group (B) urinary tumor marker comprises at least 2-hydroxy-3-methylvalerate.
3. A method for detecting a neuroblastoma, the method comprising:
   measuring a urinary tumor marker in a urine sample derived from a subject, the step including:
   measuring at least one urinary tumor marker selected from Group (A) as follows:
   (A) 3-methoxytyramine sulfate, xanthopterin, vanillactate, 3,4-dihydroxyphenylacetate, cystathionine, cortisol 21-glucuronide, 3,4-dihydroxyphenylacetate sulfate, cortisol, 3-methoxytyrosine, and 3-methoxytyramine, and
   measuring at least one urinary tumor marker selected from Group (B) as follows:
   (B) 2-hydroxy-3-methylvalerate, vanillylmandelate, homovanillate, 3-methoxy-4-hydroxyphenyl glycol, and 3-(4-hydroxyphenyl)lactate, and
   detecting a neuroblastoma in the subject based on results of the measurement,
   wherein when the at least one Group (A) urinary tumor marker is at a level higher than a reference level, it is indicated that the subject is positive for a neuroblastoma and is in a stage other than stage 4S, and
   wherein when the at least one Group (A) urinary tumor marker is at a level lower than the reference level, but the at least one Group (B) urinary tumor marker is at a level higher than a reference level, it is indicated that the subject is positive for a neuroblastoma and is in stage 4S,
   wherein the Group (A) urinary tumor marker comprises at least 3-methoxytyramine sulfate.
4. The method according to claim 1, wherein the subject is an infant under 12 months of age.
5. The method according to claim 1, wherein the detection of neuroblastoma comprises:
   detection of the presence or absence of the neuroblastoma in the subject;
   risk prediction of the neuroblastoma in the subject;
   stage determination of the neuroblastoma in the subject;
   prognosis determination of the neuroblastoma in the subject; and/or monitoring of a therapeutic effect on the neuroblastoma present in the subject.

6. The method according to claim 1, wherein the urinary tumor marker is measured by liquid chromatography-mass spectrometry (LC/MS).

7. An apparatus for detecting a neuroblastoma, the apparatus comprising:
a measuring unit which is configured to measure a urinary tumor marker in a urine sample, the measuring unit measuring:
at least one urinary tumor marker selected from Group (A) as follows:
(A) 3-methoxytyramine sulfate, xanthopterin, vanillactate, 3,4-dihydroxyphenyl acetate, cystathionine, cortisol 21-glucuronide, 3,4-dihydroxyphenylacetate sulfate, cortisol, 3-methoxytyrosine, and 3-methoxytyramine; and
at least one urinary tumor marker selected from Group (B) as follows:
(B) 2-hydroxy-3-methylvalerate, vanillylmandelate, homovanillate, 3-methoxy-4-hydroxyphenyl glycol, and 3-(4-hydroxyphenyl)lactate;
a comparing unit which is configured to compare a measured value of the urinary tumor marker measured by the measuring unit with a corresponding reference level or previous measured value; and
a determining unit which is configured to detect a neuroblastoma based on comparison results obtained by the comparing unit,
wherein, when the at least one Group (A) urinary tumor marker level is higher than the reference level or the previous measured value, the determining unit determines that the subject is positive for a neuroblastoma other than stage 4S neuroblastoma, or is at risk for the neuroblastoma, and
wherein, when the at least one Group (A) urinary tumor marker level is lower than the reference level, but the at least one Group (B) urinary tumor marker level is higher than the reference level or the previous measured value, the determining unit determines that the subject is positive for a neuroblastoma and is in stage 4S, or is at risk for the stage 4S neuroblastoma.

8. An apparatus for detecting a neuroblastoma, the apparatus comprising:
a measuring unit which is configured to measure a urinary tumor marker in a urine sample, the measuring unit measuring:
at least one urinary tumor marker selected from Group (A) as follows:
(A) 3-methoxytyramine sulfate, xanthopterin, vanillactate, 3,4-dihydroxyphenylacetate, cystathionine, cortisol 21-glucuronide, 3,4-dihydroxyphenylacetate sulfate, cortisol, 3-methoxytyrosine, and 3-methoxytyramine; and
at least one urinary tumor marker selected from Group (B) as follows:
(B) 2-hydroxy-3-methylvalerate, vanillylmandelate, homovanillate, 3-methoxy-4-hydroxyphenyl glycol, and 3-(4-hydroxyphenyl)lactate;
a comparing unit which is configured to compare a measured value of the urinary tumor marker measured by the measuring unit with a corresponding reference level or previous measured value; and
a determining unit which is configured to detect a neuroblastoma based on comparison results obtained by the comparing unit,
wherein the measuring unit measures at least three of the Group (A) urinary tumor markers and/or measures at least three of the Group (B) urinary tumor markers.

9. An apparatus for detecting a neuroblastoma, the apparatus comprising:
a measuring unit which is configured to measure a urinary tumor marker in a urine sample, the measuring unit measuring:
at least one urinary tumor marker selected from Group (A) as follows:
(A) 3-methoxytyramine sulfate, xanthopterin, vanillactate, 3,4-dihydroxyphenylacetate, cystathionine, cortisol 21-glucuronide, 3,4-dihydroxyphenylacetate sulfate, cortisol, 3-methoxytyrosine, and 3-methoxytyramine; and
at least one urinary tumor marker selected from Group (B) as follows:
(B) 2-hydroxy-3-methylvalerate, vanillylmandelate, homovanillate, 3-methoxy-4-hydroxyphenyl glycol, and 3-(4-hydroxyphenyl)lactate;
a comparing unit which is configured to compare a measured value of the urinary tumor marker measured by the measuring unit with a corresponding reference level or previous measured value; and
a determining unit which is configured to detect a neuroblastoma based on comparison results obtained by the comparing unit,
wherein the comparing unit compares a calculated objective variable resulting from multivariate analysis of the measured values of the urinary tumor marker measured by the measuring unit with a reference level obtained from a cancer examination model in the multivariate analysis, or with a previous calculated objective variable.

10. The apparatus according to claim 7, wherein the measuring unit comprises a liquid chromatograph-mass spectrometer (LC/MS).

11. A kit for detecting a neuroblastoma, the kit comprising:
a means for measuring at least one urinary tumor marker selected from Group (A) as follows:
(A) 3-methoxytyramine sulfate, xanthopterin, vanillactate, 3,4-dihydroxyphenyl acetate, cystathionine, cortisol 21-glucuronide, 3,4-dihydroxyphenylacetate sulfate, cortisol, 3-methoxytyrosine, and 3-methoxytyramine; and
a means for measuring at least one urinary tumor marker selected from Group (B) as follows:
(B) 2-hydroxy-3-methylvalerate, vanillylmandelate, homovanillate, 3-methoxy-4-hydroxyphenyl glycol, and 3-(4-hydroxyphenyl)lactate,
wherein, when the at least one Group (A) urinary tumor marker level is higher than a reference level or a previously measured value, the kit determines that the subject is positive for a neuroblastoma other than stage 4S neuroblastoma, or is at risk for the neuroblastoma, and
wherein, when the at least one Group (A) urinary tumor marker level is lower than the reference level, but the at least one Group (B) urinary tumor marker level is higher than a reference level or a previously measured value, the kit determines that the subject is positive for a neuroblastoma and is in stage 4S, or is at risk for the stage 4S neuroblastoma.

12. The kit according to claim 11,
which is a mass spectrometry reagent set.

13. A method for evaluating efficacy of a neuroblastoma therapy, the method comprising:
measuring a urinary tumor marker in a urine sample derived from an animal with a neuroblastoma, the animal having undergone a treatment with a test therapeutic agent or therapy by measuring:
at least one urinary tumor marker selected from Group (A) as follows:
(A) 3-methoxytyramine sulfate, xanthopterin, vanillactate, 3,4-dihydroxyphenylacetate, cystathionine, cortisol 21-glucuronide, 3,4-dihydroxyphenylacetate sulfate, cortisol, 3-methoxytyrosine, and 3-methoxytyramine, and at least one urinary tumor marker selected from Group (B) as follows:
(B) 2-hydroxy-3-methylvalerate, vanillylmandelate, homovanillate, 3-methoxy-4-hydroxyphenyl glycol, and 3-(4-hydroxyphenyl)lactate, wherein at least three of the Group (A) urinary tumor markers and at least one of the Group (B) urinary tumor markers are measured; and
evaluating efficacy of the test therapeutic agent or therapy on the neuroblastoma based on the measurement results.

* * * * *